United States Patent [19]

Stimpson

[11] Patent Number: 5,562,918
[45] Date of Patent: Oct. 8, 1996

[54] DRUG DISPENSING SYSTEM

[75] Inventor: Philip G. Stimpson, Welford, United Kingdom

[73] Assignee: Bespak PLC, Norfolk, United Kingdom

[21] Appl. No.: 392,921

[22] PCT Filed: Sep. 1, 1993

[86] PCT No.: PCT/GB93/01851

§ 371 Date: Mar. 1, 1995

§ 102(e) Date: Mar. 1, 1995

[87] PCT Pub. No.: WO94/05358

PCT Pub. Date: Mar. 17, 1994

[30] Foreign Application Priority Data

Sep. 5, 1992 [GB] United Kingdom ............ 9218852

[51] Int. Cl.⁶ .................... A61K 9/48; A61M 15/00
[52] U.S. Cl. ............... 424/451; 128/200.24; 604/890.1
[58] Field of Search .......... 424/451; 604/890.1; 128/200.24

[56] References Cited

U.S. PATENT DOCUMENTS

| 2,307,986 | 1/1943 | Bolté et al. ............ 604/58 |
| 2,672,144 | 3/1954 | Cohen ................... 604/58 |

FOREIGN PATENT DOCUMENTS

| 0129985 | 1/1985 | European Pat. Off. . |
| 1499518 | 9/1967 | France . |
| 2352556 | 12/1977 | France . |
| 8807025 | 7/1988 | Germany . |
| 1103969 | 2/1968 | United Kingdom . |
| 1108629 | 4/1968 | United Kingdom . |
| 1436028 | 5/1976 | United Kingdom . |
| 2193637 | 2/1988 | United Kingdom . |
| 2246299 | 1/1992 | United Kingdom . |
| 2253200 | 9/1992 | United Kingdom . |
| 2255918 | 11/1992 | United Kingdom . |
| WO89/01348 | 2/1989 | WIPO . |
| WO89/02289 | 3/1989 | WIPO . |

*Primary Examiner*—D. Gabrielle Phelan
*Attorney, Agent, or Firm*—Beveridge, DeGrandi, Weilacher & Young, L.L.P.

[57] ABSTRACT

A drug capsule comprises a sleeve forming a side wall of the capsule and having first and second end caps which close the opened ends of the sleeve. The end faces of the end caps are frangible so that they can be ruptured by the open ends of the sleeve by causing the end caps to be displaced along the sleeve towards one another to open the capsule. A dispenser is formed from the combination of the capsule and a pair of elements, each element being adapted to receive a respective one of the end caps so that the capsule interconnects the elements, whereby the capsule can be opened by moving the elements towards one another. One of the elements provides a mouth piece and the other element provides an air flow passageway provided with a turbine to induce turbulence in the air flow through the capsule. The drug capsule and dispenser are primarily intended for administering powdered drugs by inhalation.

10 Claims, 9 Drawing Sheets

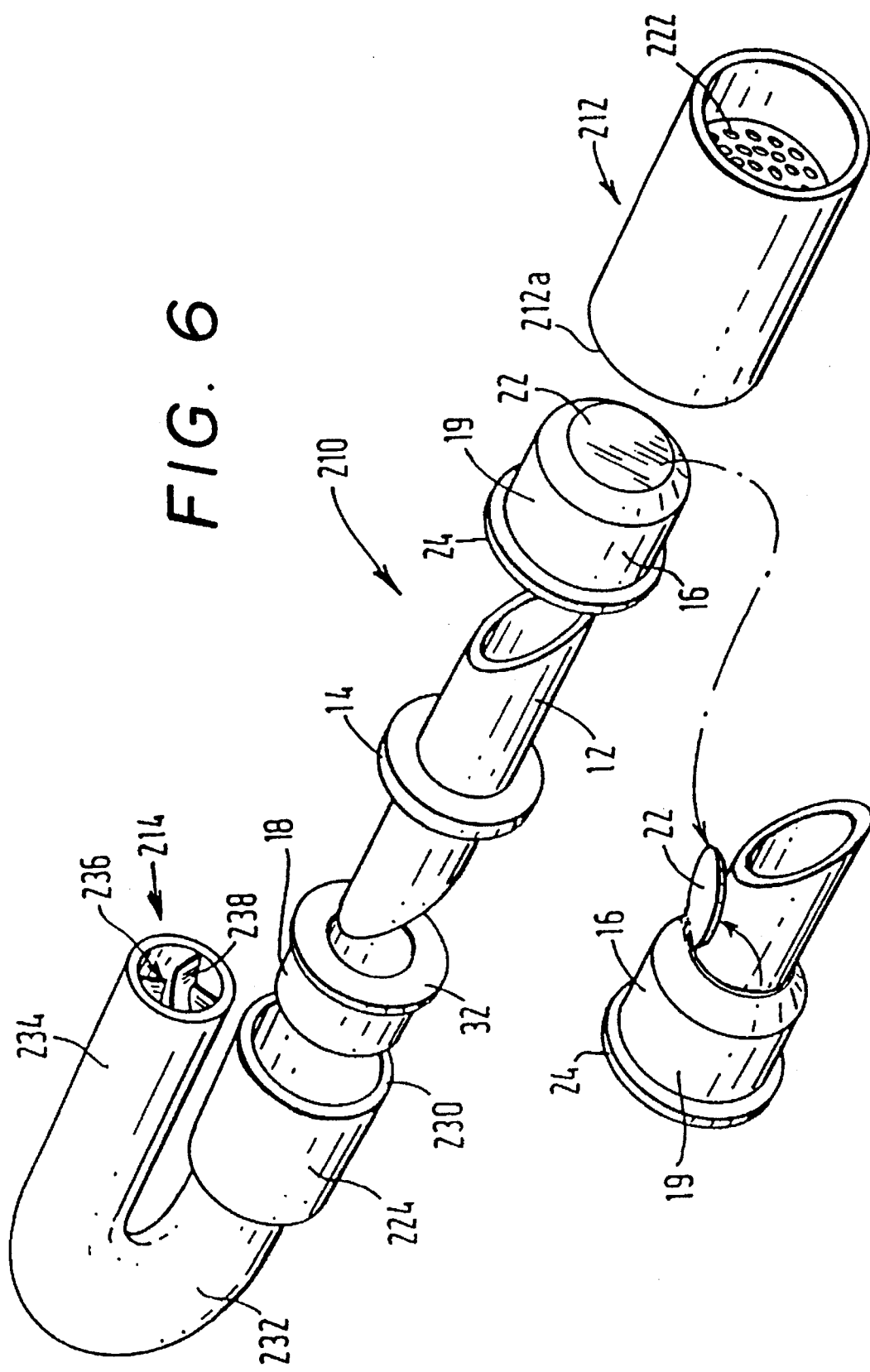

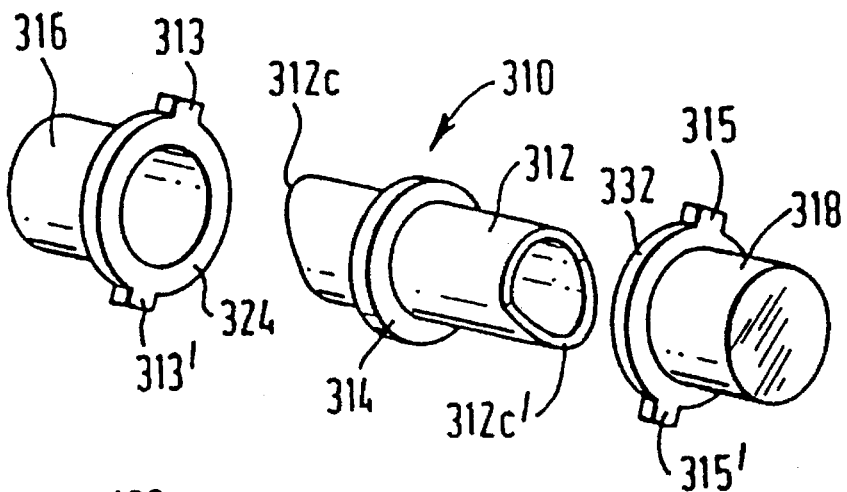
FIG. 11
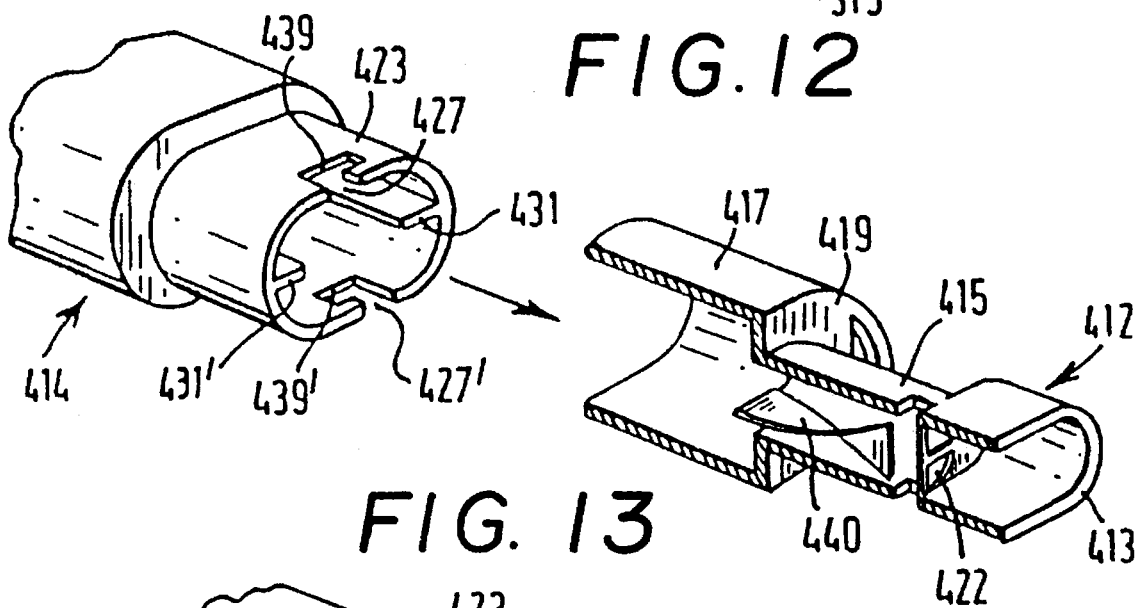
FIG. 12
FIG. 13
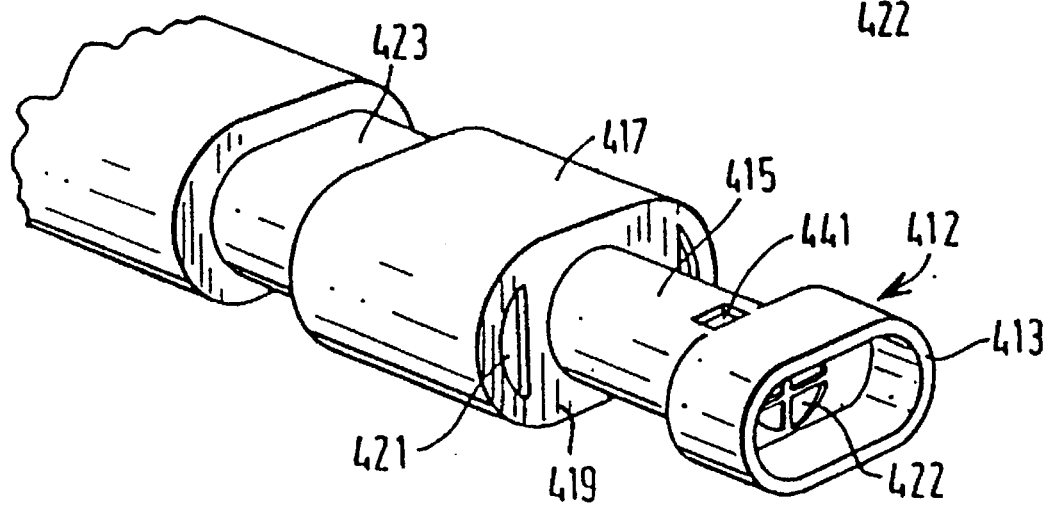

FIG. 17
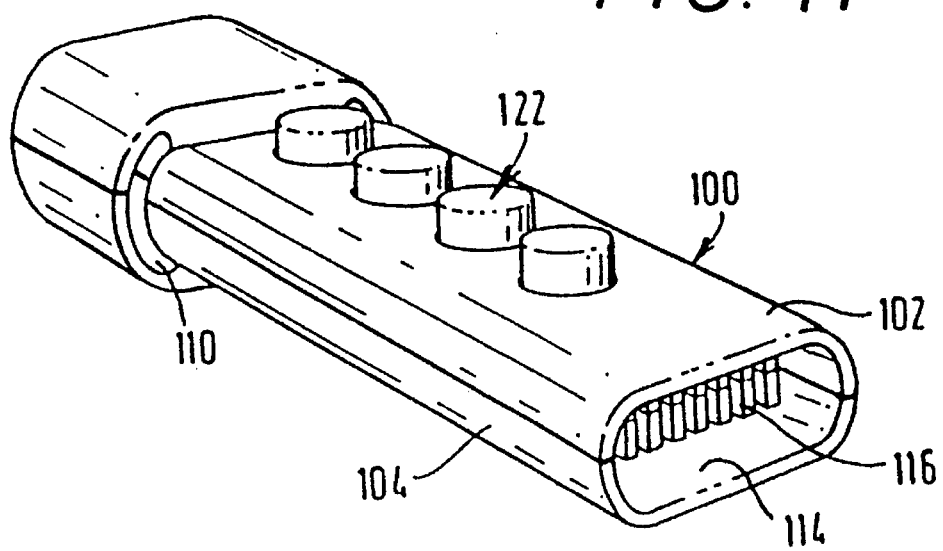
FIG. 17a
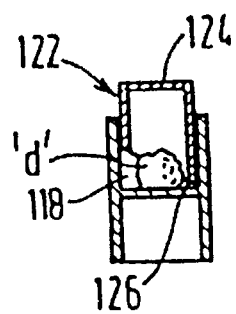
FIG. 18
FIG. 19
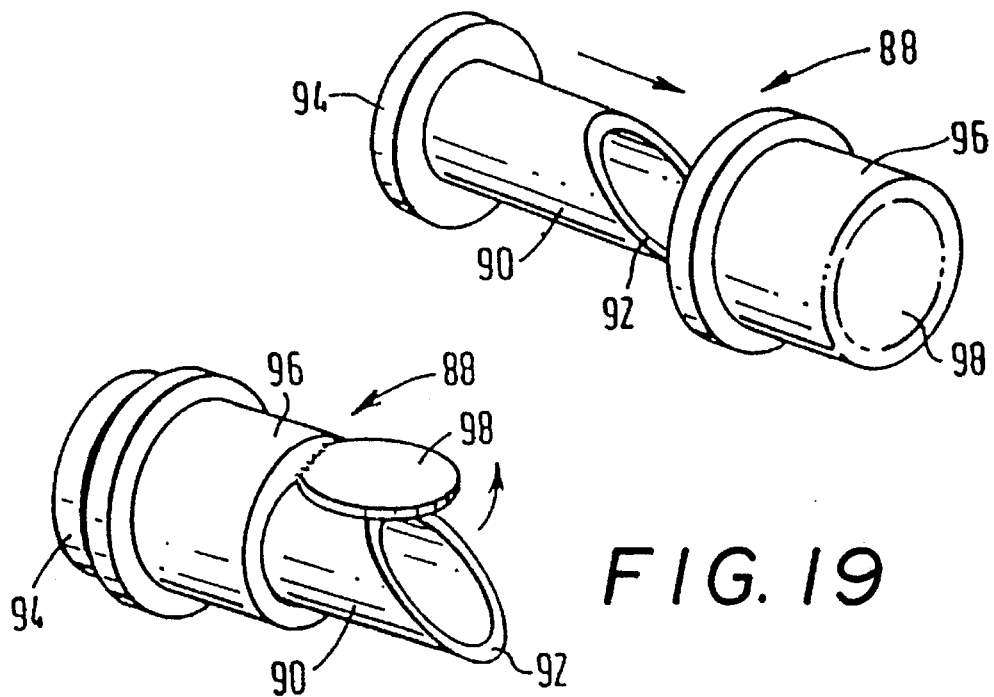

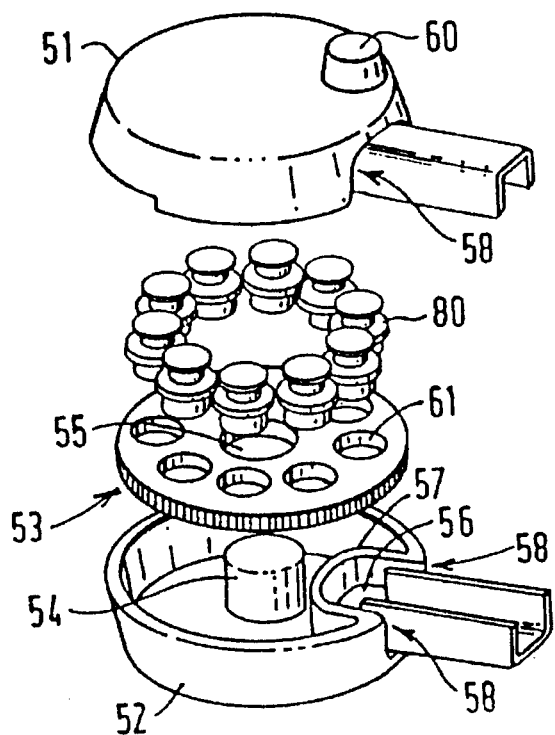
FIG. 20
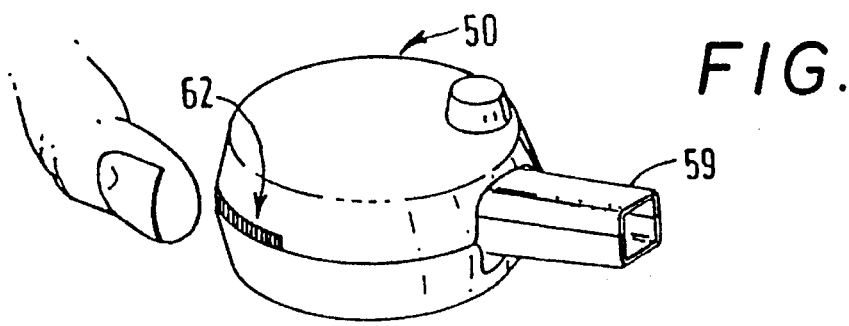
FIG. 21
FIG. 22
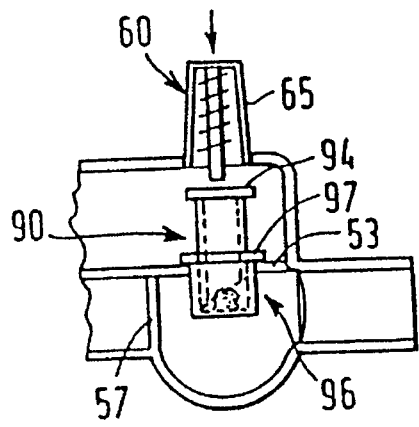
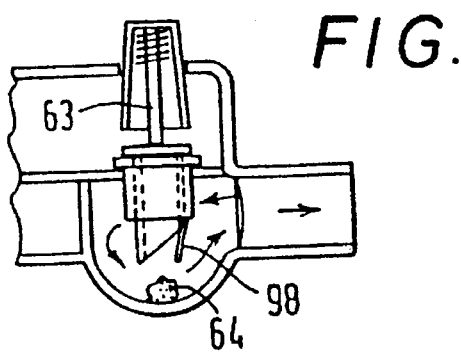
FIG. 23

DRUG DISPENSING SYSTEM

This invention relates to a drug dispensing system which is particularly useful for administering powdered drugs by inhalation. The drug dispensing system comprises a drug dispenser and a drug capsule, each of which is individually included in the invention.

In one aspect, therefore, this invention relates to a drug capsule which is particularly useful for a powdered dose form of medicine which is administered by inhalation. Thus the capsule of the present invention normally would be non-soluble and not intended to be consumed. The capsule is intended for use as a drug cartridge which can be ruptured at such time as administration is required whereby the drug can be readily and efficiently extracted from the capsule.

In known powder dose inhalation devices it is common to use known capsules which comprise a soluble case of gelatin which encloses a dose of medicine. Such capsules are inserted in an inhaler device either as a single dose or in an array for multiple dose usage and, at the appropriate time, when a patient requires the powdered dose to be administered, the capsule is pierced or sheared whereafter the patient inhales to entrain the powder dosage of medicine in a stream of inhaled air.

In one aspect of the invention, there is provided a drug capsule comprising a member which can be ruptured to open the capsule and a member which may be moved relative to the rupturable member to rupture it.

Preferably the movable member is adapted to rupture the rupturable member by at least partially severing it to form a disc of material. The rupturable member suitably comprises an end face of the capsule.

Preferably the movable member comprises a sleeve forming a side wall of the capsule and having first and second ends and the rupturable member comprises a displaceable end cap closing the first end of the sleeve, the end cap having an end face which can be ruptured by the end of the sleeve by urging the end cap against the end of the sleeve. The first end of the sleeve preferably comprises an ellipse the plane of which is at an angle to the plane normal to the axis of the sleeve so as to form a cutting edge which can cut progressively through the end face of the end cap. The end cap is preferably displaceably connected to the sleeve by a rib and groove connection. The end face of the end cap preferably remains hinged to the end cap after being ruptured and displaced along the sleeve.

In some embodiments wherein the movable member comprises a sleeve, the second end of the sleeve is closed by a rupturable and displaceable end cap in like manner to the first end and the sleeve is preferably provided with an outwardly projecting flange or other stop means intermediate its ends, against which the end caps abut when fully displaced along the sleeve from its ends. In other embodiments, the second end of the sleeve is closed by means not displaceable relative to the sleeve in normal use, for example a cross wall integral with the sleeve.

In a second aspect there is provided a drug capsule for a powder inhaler, comprising a tubular side wall having a first, open end and, displaceably connected to the side wall, an end cap closing the first end of the side wall, the end cap having a body portion and an end wall portion at least partially severable from the body portion and the first end of the side wall having a cutting edge partially to sever the end wall portion from the body portion when the end cap is urged against the first end of the side wall to form a disc hinged to the body portion. The end cap is preferably provided with a flange or other abutment means projecting therefrom in a radial direction. In some embodiments, the tubular side wall has a second open end like the first and closed by a displaceable end cap like that closing the first end and the side wall is provided with an outwardly projecting flange or other stop means intermediate its ends against which the end caps abut when fully displaced along the sleeve from its ends.

In other embodiments, the tubular side wall has a second end closed by an integral end wall or other means not displaceable with respect to the side wall in normal use.

The invention further includes a drug capsule comprising a hollow body whose opposite ends are frangible relative to the body so that the capsule can be ruptured at its ends to extract the drug dosage contained therein. Each of the opposite ends of the capsule preferably comprises an end face which is frangible and can be at least partially severed from the body to form a disc of material. The hollow body suitably comprises a sleeve whose open ends are closed by a pair of opposite end caps displaceably connected to the body, the end faces of the end caps being frangible so that they can be ruptured by the ends of the sleeve by causing the end caps to be displaced along the sleeve body towards one another.

Another aspect of the invention provides a drug dispenser formed from the combination of a drug capsule of the invention openable at its opposite ends and a pair of pipe elements, the pipe elements each being adapted to receive a separate one of the end caps of the capsule so that the capsule interconnects the pipe elements, and wherein one of the pipe elements provides a mouth piece and the capsule can be ruptured by moving the pipe elements towards one another whereby the ruptured capsule provides a part of an air flow passageway of the dispenser so that the drug dose contained within the capsule can be inhaled through the mouth piece.

The capsules of the invention are preferably formed from a plastics material.

Drug capsules of the invention which are adapted to open at opposed ends (so that they may form part of the airflow passageway of an inhaler) may include turbulence inducing means (e.g. a baffle or stationary turbine) to help entrainment of drug in the capsule. Drug capsules adapted to be opened at both ends and comprising turbulence inducing means are included in the invention.

According to yet another aspect of the invention, there is provided a drug capsule comprising a pair of hollow bodies each of which has an open end and an opposite closed end and which fit together to form a closed capsule, and wherein the closed end of one of the bodies is frangible, the bodies being movable with respect to one another such that the the frangible closed end of the one of the bodies is ruptured by the open end of the other of the bodies thereby allowing the drug dosage contained within the capsule to be extracted.

According to a still further aspect of the invention, there is provided a drug dispenser incorporating at least one drug capsule according to the immediately preceding paragraph, in which the one body is provided by a casing part of the dispenser in which the other body is slidably received and wherein the frangible closed end of the one body is disposed so that, when ruptured, a drug dosage is released into a passageway of the dispenser, the passageway communicating with a mouthpiece by which the released dosage can be administered to a patient.

This invention includes a drug dispenser which is particularly useful for administering powdered drugs by inhalation. In a preferred form, the dispenser is adapted to be utilised with a drug capsule of the invention.

This dispenser seeks to improve the efficiency of solid dose drug administration, to avoid complex delivery mechanisms and offer a patient ease of use with minimal effort.

The invention accordingly provides an inhalation device comprising an air inlet, an air outlet, means in use holding or forming a drug carrier which contains a drug and comprises two or more parts which are relatively linearly movable to cause rupturing of the carrier to allow the drug to be inhaled from a chamber intermediate and in communication with the air inlet and the air outlet, the device being provided with an abutment surface whereby linear force may be applied to a drug carrier to cause movement of its movable parts and rupture of the carrier.

In first embodiments the chamber is formed by the drug carrier, which can be ruptured at both ends to form part of an airflow passageway through the device. The drug carrier holding or forming means is in some inhalation devices adapted to hold a drug carrier and the abutment surface is arranged to abut an abutment surface of a drug carrier held by the holding means; preferably, such inhalation devices further comprise a second abutment surface facing towards said first abutment surface, the first and second abutment surfaces being relatively linearly moveable and the drug carrier holding means being adapted to hold a drug carrier between the first and second abutment surfaces, whereby the first and second abutment surfaces may be moved relatively towards each other to abut a drug carrier held in the device and urge the moveable pans thereof to move and cause rupturing thereof.

In inhalation devices comprising a second abutment surface, the drug carrier holding means suitably comprises recesses facing towards each other to receive opposite ends of a drug carrier, the opening of each recess being defined by a respective one of the first and second abutment surfaces. Such devices preferably comprise a mouth piece comprising the first abutment surface and a tail piece comprising the second abutment surface, which pieces are movable towards and away from one another; the mouth piece and the tail piece may be adapted to interengage to define a chamber to receive a drug carrier held by the device.

In second embodiments, the chamber is defined in the device which thereby has defined therein an airflow passageway comprising the air inlet, the chamber and the air outlet, and wherein the drug carrier holding or forming means in use hold or form a drug carrier which releases a drug into the chamber when ruptured.

In some of the second embodiments, the drug carrier holding or forming means is adapted to hold a drug carrier and the abutment surface is arranged to abut an abutment surface of a drug carrier held by the holding means. In others of the second embodiments, the drug carrier holding or forming means forms a drug carrier and comprises a moveable part on which is provided the abutment surface of the device, the part being moveable by application of force on the abutment surface to cause rupture of the carrier.

Devices according to the second embodiment preferably further comprise a button or other movable member opposite to apply force in a direction towards the abutment surface of the holding means against a drug carrier held by the holding means to cause rupture of the carrier. The devices are desirably adapted for force to be applied to a drug carrier the holding means directly by a finger or thumb. Also in devices of the second embodiment the holding means suitably comprises a recess whose opening is defined by the abutment surface of the device.

In the inhalation devices according to the invention, the drug carrier holding or forming means in use forms or holds a plurality of drug carriers. The drug carrier holding or forming means is preferably moveable such that in use the drug carriers may be brought sequentially into a position where they may be ruptured by the application of force to allow the drug in the carrier before rupture to be inhaled and they may comprise a rotary carousel.

In a further aspect, there is provided a drug dispenser of the type in which a drug is administered to the patient by inhalation through the device, said dispenser having a mouth piece and a tail piece comprising an airflow passageway and adapted to receive between them a drug carrier, said mouth piece and said tail piece being movable towards one another relative to said drug carrier and comprising abutment means to abut the drug carrier such that continued movement of the mouth piece and the tail piece towards one another after they have abutted the drug carrier ruptures the drug carrier so that the drug contained therein can be inhaled through the mouth piece.

The mouth piece and the tail piece of the drug dispenser are preferably adapted to receive between them a drug carrier which, when ruptured by relative movement of the said pieces constitutes a portion of the air flow passageway through the dispenser. The mouth piece is suitably adapted to receive one end of the drug carrier and the tail piece is adapted to receive the opposite end of the drug carrier in substantial axial alignment. The tail piece may include an end part which forms an elbow in the air flow passageway of the dispenser so that material from the drug carrier is not lost through the open end of the tail piece.

In the drug dispenser, the mouth piece and the tail piece are preferably adapted to interengage to define a chamber to receive a drug carrier. In preferred embodiments of such dispensers the mouth piece and the tail piece of the drug dispenser are preferably adapted to receive between them a drug carrier which, when ruptured by relative movement of the said pieces, constitutes a portion of the air flow passageway through the dispenser and the chamber has one or more air inlet ports disposed nearer to the outlet of the chamber than is the end distal to the outlet of a received drug carrier, the chamber being designed for an airflow passageway to be defined between the air inlet port(s) and said distal end of a received drug carrier and for there to be substantially no airflow passageway between the air inlet port(s) and the chamber outlet. Suitably, the chamber has a dome-shaped end wall in the tail piece, which serves to induce turbulence in air flowing from the air inlet port(s) to said distal end of a received drug carrier.

It is a preferred feature of inhalation devices and drug dispensers according to the invention that means are provided to induce turbulence in air passing through the apparatus before, or as, it entrains a drug made available by rupture of a drug carrier; such means are therefore normally disposed upstream of the site where the drug becomes available, e.g. in the tail piece of a drug dispenser of the invention.

It is another preferred feature that inhalation devices and drug dispensers of the invention include means to induce turbulence in air after it has entrained a drug. Such means are therefore disposed downstream of the location at which drug becomes available to entrainment.

Preferred embodiments include a grill in the airflow passageway downstream of the location where drug becomes entrained and usually close to the outlet, after any turbulence inducing means.

The invention also includes an inhalation device having defined therein an airflow passageway between an air inlet and an air outlet, the airflow passageway comprising intermediate the inlet and outlet a chamber to receive a drug powder and the device comprising a holder for a drug capsule disposed above the chamber, the device either being adapted for a user's finger or thumb to have access to a drug capsule in the holder or comprising means provided with an abutment surface and operable to apply force to a drug capsule in the holder with the abutment surface, to rupture the capsule and release a drug contained therein into the chamber. The holder may be in the form of a rotary carousel for a multiplicity of (e.g. 5 or more) drug capsules, the carousel normally being adapted to be rotated to dispose the drug capsules above the chamber in turn.

Further included is an inhalation device having defined therein an airflow passageway between an air inlet and an air outlet, the airflow passageway comprising intermediate the inlet and outlet a chamber to receive a drug powder and the device comprising a drug cartridge comprising an upstanding displaceable member which, upon downward displacement, ruptures a drug capsule in the cartridge to release drug powder contained therein into the capsule, the device either being adapted for a user's finger or thumb to have access to the displaceable member or comprising means provided with an abutment surface and operable to apply force to the displaceable member to rupture the capsule. The cartridge may be in the form of a rotary carousel comprising a multiplicity of (e.g. 5 or more) drug capsules, each with an associated displaceable member, the carousel normally being adapted to be rotated to dispose the drug capsules above the chamber in turn.

The invention additionally provides an inhalation device adapted to hold a drug carrier, which drug carrier comprises two or more parts which are relatively linearly movable to cause rupturing of the carrier, the inhalation device comprising stop means against which a drug carrier may be urged to cause relative movement of the carrier's parts and rupture of the carrier.

Included in the invention is a powder inhaler in which a drug capsule is ruptured at opposed ends to become part of the airflow passageway between the air inlet and air outlet of the inhaler or in which drug powder is discharged from a drug capsule by removal of an end wall or a substantial portion of an end wall of the capsule from a state in which it closes the capsule to one in which it does not impede discharge of the drug powder.

Also included is the use, to provide an orifice for discharge of drug powder from a powder inhaler drug capsule, of an end wall of which at least a substantial portion is adapted for removal as a disc from its position as an end wall of the capsule to one in which it does not impede discharge of the drug powder, as well as a drug capsule adapted for removal of at least a substantial portion of an end wall thereof (and optionally of each opposite end wall thereof) from its position as an end wall of the capsule to one in which it does not impede discharge of the drug powder. The formation of an orifice by removal of a disc from the wall may be distinguished from formation of an orifice by piercing a capsule.

Further provided is a drug capsule adapted for removal as a unit of a wall portion thereof (e.g. an end wall portion) from its position as a wall portion of the capsule to a position in which it does not impede discharge of the drug from the capsule. The wall portion may be part of an end cap of the capsule, e.g. an end cap displaceably connected to the capsule. The capsule is preferably adapted for the wall portion to be removed as a disc of material remaining associated with the capsule through a hinge. The wall portion is preferably removed by movement relative to the portion of another portion of the capsule.

BRIEF DESCRIPTION OF THE DRAWINGS

Embodiments of non-consumable drug capsules and drug dispensing devices according to the invention will now be described, by way of example, with reference to the accompanying drawings, in which:

FIG. 6 is a schematic exploded perspective view of a drug dispenser according to the invention shown together with a drug capsule;

FIG. 7 is a perspective view of one end of a drug capsule which has been opened;

FIG. 11 is an exploded view of a further drug carrier embodying the invention;

FIG. 12 is an exploded and partially sectional schematic illustration of a drug dispenser adapted for use in the drug carrier of FIG. 11;

FIG. 13 is a perspective view of the drag dispenser of FIG. 12, showing the mouth piece and tail piece in engagement;

FIGS. 16 and 17; 16a and 17a are perspective and cross-sectional views respectively of a drug dispensing device incorporating a drug cartridge in which only a single end is ruptured;

FIGS. 18 and 19 are perspective views of another drug capsule according to the invention, in which only a single end of the capsule is adapted to be raptured;

FIG. 20 is an exploded perspective view of a drug dispenser incorporating a carousel useful with the capsules of FIGS. 18 and 19;

FIG. 21 is a perspective view of the dispenser of FIG. 20;

FIGS. 22 and 23 are partial sectional views through the dispenser of FIG. 20;

Figures 1, 2:
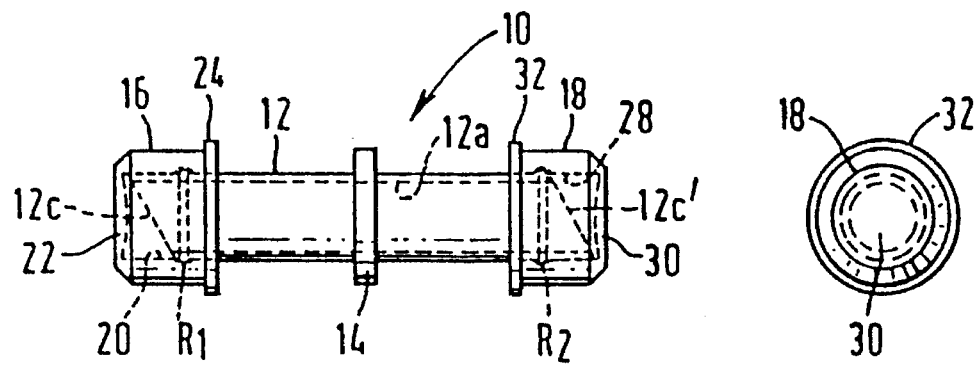
FIG. 1 is a side elevation of a capsule in its completed form providing a drug carrier.
FIG. 2 is an end view of the capsule of FIG. 1.

Referring to the drawings, the capsule 10 is formed from a suitable plastics material and is typically of the order of size of known consumable gelatin drug capsules. It is envisaged that the typical capsule can be produced on existing equipment although some modification may be required. The capsule 10 comprises a central hollow elongate cylindrical sleeve 12 including a smooth through bore 12a and having a radially extending central external flange 14. Although the body of the capsule is of annular cross section in this embodiment other body shapes and/or cross sections are envisaged, for example, square or ovate cross sections. The body 12 is, of course, intended to contain a dose of medicine, usually although not necessarily in powder form. The ends of the open-ended body 12 are initially closed by a pair of similar end caps 16 and 18 respectively. End cap 16 is a cup shaped body of hollow cylindrical form having an internal blind bore 20 which is closed by a frangible end face or base 22 of the end cap. At its opposite end the end cap is formed with a radially extending annular flange 24. Internally of the end cap, intermediate its ends, an annular groove 26 is provided in the bore 20 adjacent radial flange 24. End cap 18 is of similar form and includes an internal blind bore 28, frangible end face 30, radial flange 32 and internal annular groove 34.

Referring now to sleeve body 12, the ends of the sleeve are cut in each case to form an ellipse, the ellipse being contained in a plane which lies at an angle to the normal of the axis of the sleeve. The planes of the ellipses at each of the opposite ends of the sleeve are arranged to be parallel to one another. This construction produces a cutting edge 12c, 12c' at each of the opposite ends of the sleeve which in each case is able to pierce and progressively cut into the frangible end face of the adjacent end cap when force is applied to that end cap in a direction to shift it towards the central flange 14.

Figure 3:
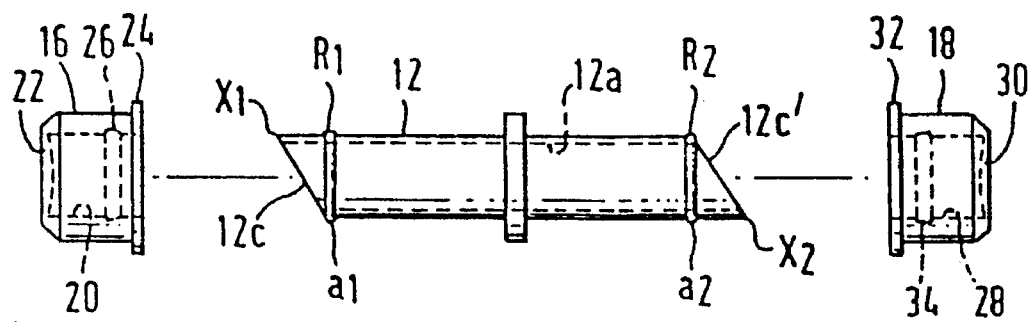
FIG. 3 is an exploded view of the capsule of FIG. 1 showing a central body portion and two opposite but similar end caps.

The end caps are normally held in a position in which they seal the respective ends of the sleeve by cooperation between the internal groove and an annular radially extending rib $R_1$, $R_2$ respectively formed adjacent to each end of the sleeve. The angle of each cutting edge 12c, 12c' of the sleeve end face relative to the adjacent rib is chosen so that the axial position of the plane containing the rib on the sleeve coincides with that part of the tangent to the cutting edge which is closest to the central flange 14, i.e. at positions $a_1$ and $a_2$ respectively as seen in FIG. 3.

Figures 4, 5:
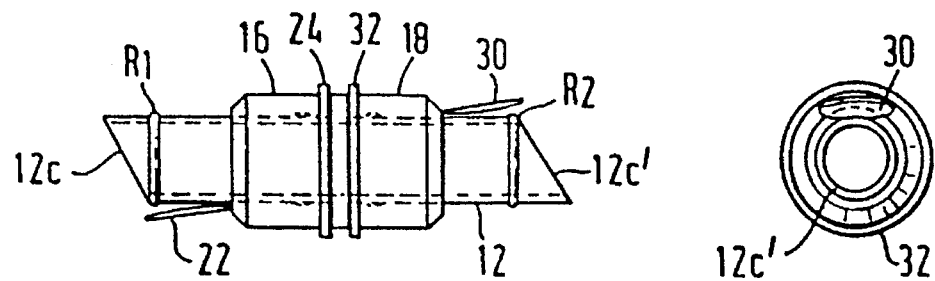
FIG. 4 is a side elevation of the capsule of FIG. 1 shown after it has been opened with its end caps ruptured and displaced along the central body portion towards one another.
FIG. 5 is an end view of the capsule of FIG. 1 as seen from one end of FIG. 4.

The end caps 16 and 18 normally are located to seal the ends of the sleeve body and to this end the internal annular groove 26, 34 of each end cap cooperates with the respective rib $R_1$, $R_2$ so that the axial extremity of each cutting edge $X_1$, $X_2$, is disposed at or closely adjacent to the frangible end face of the respective end cap. An axial force applied to each end cap towards its opposite end cap sufficient to dislodge the engagement between the groove and rib will cause the frangible end face 22, 30 to be ruptured by the adjacent cutting edge 12c, 12c' which will then progressively cut through the end face along an arcuate line of cut as the end cap is displaced axially towards the flange 14 of the sleeve body. When the end caps are fully displaced so that flanges 24 and 32 are brought into abutment with the central flange 14 or at least closely adjacent the flange 14, then the frangible end faces 22 and 30 will have been cut out to form a disc of material which preferably remains hinged to the respective end cap as shown in FIGS. 4 and 5.

Thus, as the body of the sleeve passes through the end face of the end cap the disc is displaced to lie along the circumferential wall of the sleeve. Since the cutting edges 12c, 12c' are disposed in planes which are parallel to one another then at one end of the capsule when it is opened the disc of material will be displaced downwardly whereas the other opposite disc of material will be displaced upwardly, as seen in side elevation.

Of course, when the capsule has been opened by displacing the end caps towards one another then an air flow passageway is created so that the powdered material can be drawn from within the sleeve without any ruptured part of the capsule lying in the path of the air stream. It is an advantage that the displaced frangible end faces of the end caps remain hinged to the end caps so that they do not become entrained in the air flow when inhalation of the drug dosage is in progress.

It is envisaged that other forms of capsules can be adopted and indeed in its most basic form the objectives of the invention may be met by providing a capsule whose opposite ends are frangible relative to, or frangibly connected to, the body of the capsule so that they can be readily ruptured by some suitable means. For example, the capsule may have integral but frangible end faces to be ruptured by some suitable means or the capsule may be formed with an annular line of weakness adjacent each end thereof so that the ends can readily be at least partially severed from the body.

Referring to the FIGS. 6 to 11, there is shown a drug dispenser useful for utilisation with a drug capsule of the invention. The dispenser 210 which comprises a mouth piece 212 and a tail piece 214 adapted to receive between them a sealed drug capsule which is loaded with e.g. a drug dosage in powdered form for administration to a patient by inhalation through the mouth piece. For this purpose a suitable drug capsule is a capsule as described with reference to FIGS. 1 to 5. The end caps are ruptured by displacing them towards one another along the body of the capsule to open the ends of the capsule so that the drug dosage can then be extracted.

The mouth piece 212 of the dispenser is of hollow cylindrical form and is adapted to receive in one of its open ends 212a one of the end caps 16 of the drug capsule and is sized so that the cylindrical body 19 of the end cap can be fully received in the open end 212a of the mouth piece such that the radial end flange 24 of the end cap abuts against the axial end face of the mouth piece. Internally the mouth piece is formed with a perforate grill 222 adjacent the opposite end thereof. The grill 222 is provided in order to break up by impact any of the particulate matter which as formed into unacceptably large lumps or clusters.

The opposite tail end 214 of the device includes a first cylindrical portion 224 which is similar to the mouth piece in that it is adapted to receive the opposite end cap 18 of the drug capsule and is sized to receive the end cap so that the radial end flange 32 of the end cap abuts against the annular end face 230 of the cylindrical portion 224. The tail piece also includes an end pipe 232 which is turned through 180 degrees relative to the axis of cylindrical portion 224 to form an elbow and terminate in an end part 234 which has its axis lying parallel to the main axis of the device. The end pipe is turned through 180 degrees in this manner so that, when the drug capsule is ruptured, the powdered drug dose cannot escape through the open end of the tail piece of the device.

In this construction the powdered drug will, if the device is held incorrectly, deposit in the bend between the end piece and the cylindrical portion but is still able to be inhaled through the mouth piece. In order to create better conditions for turbulent air flow through the device a fixed blade turbine 236 may be provided in the open-ended tail piece. The turbine 236 comprises a plurality of radially inwardly directed fixed blades 238 helically twisted along their lengths. Other forms of turbulence inducing devices may of course be incorporated in the device.

In order to operate the device so that the drug capsule is ruptured whereby its contents can be entrained in an air flow, created by a patient's inhalation, it is simply necessary to move the mouth piece and tail piece towards one another so that they meet at the central flange 14 of the main body 12 of the drug capsule. In so doing of course force is transmitted through the flanges of the end caps of the drug capsule to cause the end caps themselves to be displaced along body 12 towards one another until those flanges also are in abutment with or close to the central flange 14 of the capsule. This displacement causes the end faces 22, 30 of the end caps to be cut away by the end cutting edges 12c, 12c' so that the capsule has both its opposite ends opened to allow for the inhalation of the drug dosage from within the capsule through the mouth piece of the device.

FIG. 7 shows the situation at either one of the ends of the drug capsule after the end cap has been displaced along the body of the capsule to allow for the release of the powdered dosage. The end face of the end cap is normally cut to form a hinged lid as shown in the Figure. Thus, the ends of the capsule are fully opened to allow uninterrupted flow while at the same time the cut end face is not released to become entrained in the air flow.

Figure 8:
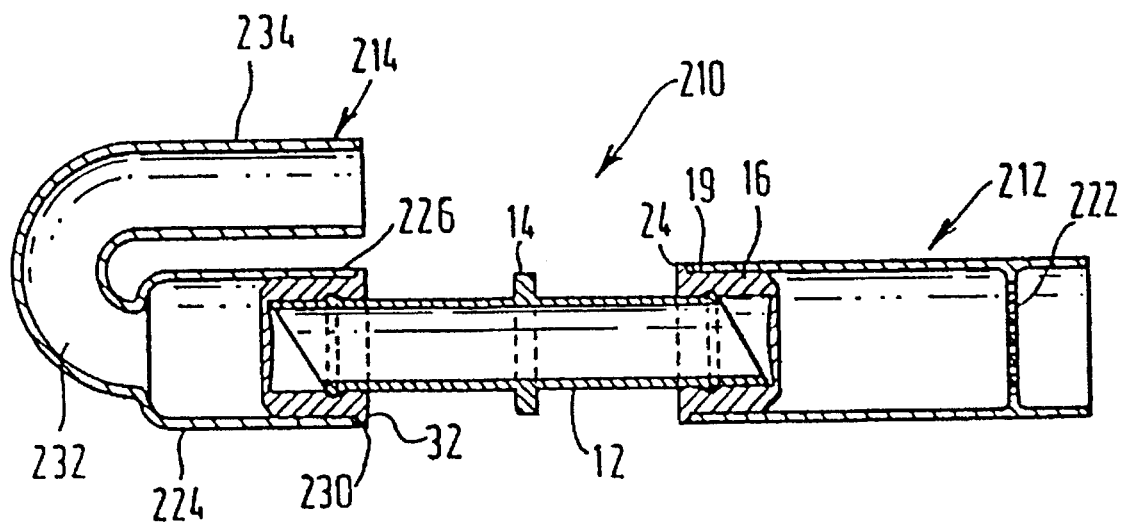
FIG. 8 is a vertical cross-section through a drug dispenser which incorporates a drug capsule and is shown in a condition in which the dispenser is charged ready for use.
Figure 9:
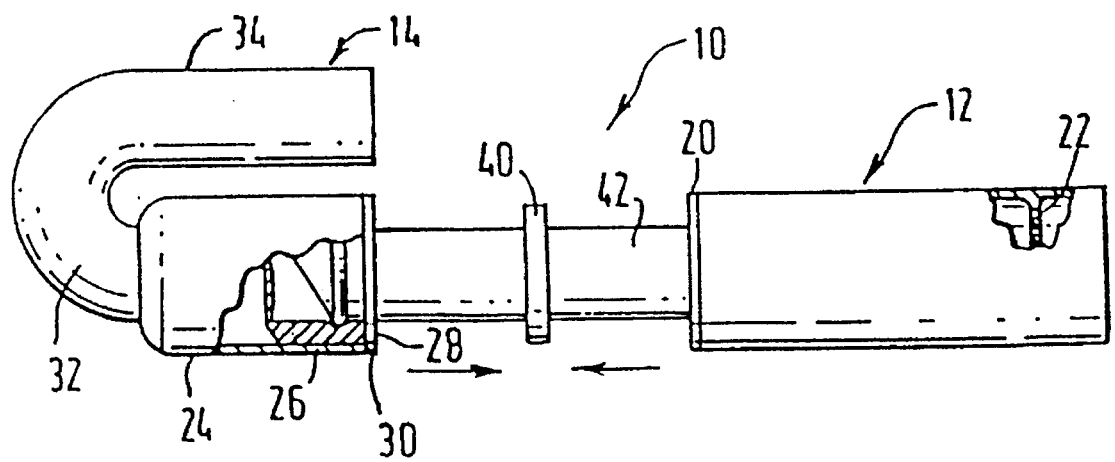
FIG. 9 is a side elevation of a dispenser charged ready for use and shown in partial cross-section.
Figure 10:
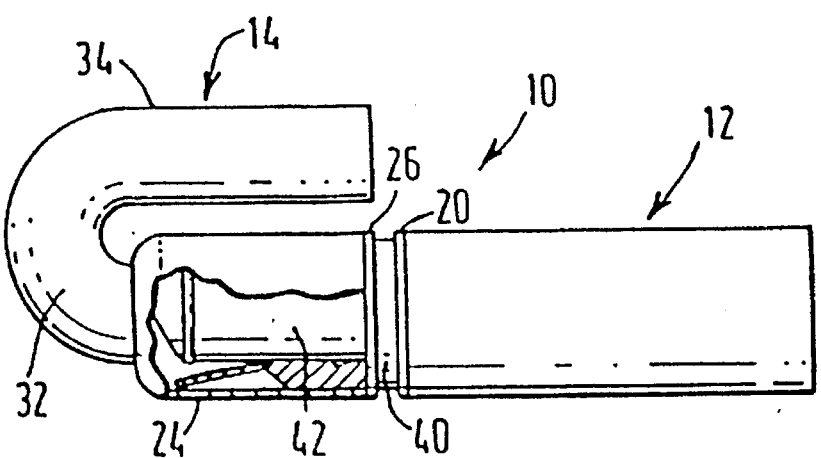
FIG. 10 is a side elevation of a dispenser shown partly in cross-section after use in which the drug capsule has been ruptured.
Figure 14:
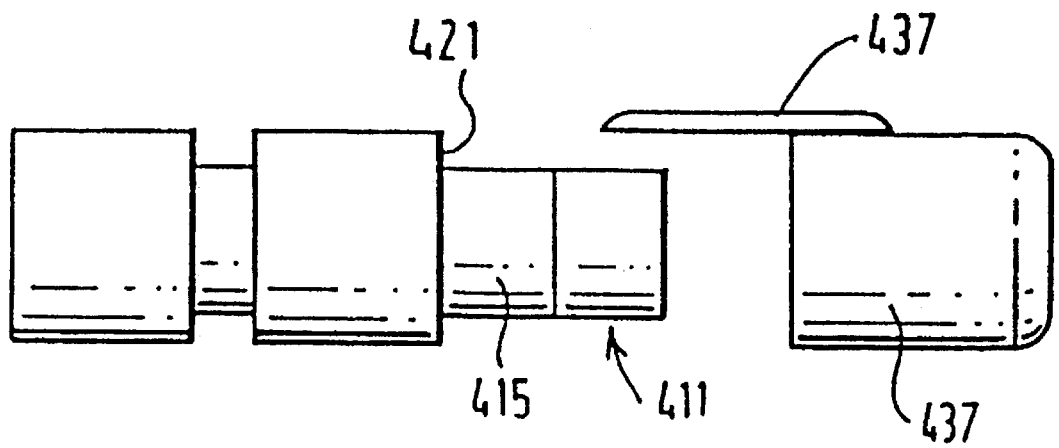
FIG. 14 is a side view of the drug dispenser of FIG. 12 showing a cap for the dispenser.

The relative position of the body of the capsule within the mouth piece and tail piece after the end caps have been displaced along the body of the capsule is shown in broken lines in FIG. 8.

In this arrangement therefore the drug capsule when opened acts as a part of the air flow passageway of the device.

FIG. 11 illustrates in an exploded view a modified embodiment of the drug capsule, intended for use in the embodiment of the drug dispenser illustrated in FIGS. 12 to 15.

The drug capsule 310 of FIG. 11 comprises a central cylindrical body 312 similar to that illustrated in FIGS. 1 to 5. The body 312 therefore includes a through bore and an outwardly extending central flange 314, which may optionally be discontinuous. The ends of the body 312 are cut to form an ellipse as in FIG. 1 or, as shown in FIG. 11, are formed with an arcuate portion of the body 312 extending axially to define a semi-ellipse lying at angle to the perpendicular. In this way, a cutting edge 312c, 312c' is formed at each end of the body 312, the cutting edges 312c, 312c' normally being in diametrically opposed relationship as shown.

The capsule 310 further comprises end caps 316 and 318. For clarity, the end caps 316, 318 are shown separated from the body 312 in the exploded view of FIG. 11. However, in the complete capsule 310 the end caps 316, 318 are seated over the open ends of the body 312. The end caps are of similar structure to the end caps 16, 18 of the embodiment of FIGS. 1 to 5 but, in addition, comprise radially extending lugs 313, 313' and 315, 315' projecting from radial flanges 324, 332.

FIGS. 12 to 15 illustrate a dispenser adapted for use with the drug capsule 310 of FIG. 11. The dispenser in cross section is generally not circular but a rounded oblong or a flattened, elongate oval.

The dispenser has a mouth piece 412 which comprises an oblong outlet portion 413 to be held in a patient's mouth and accomodating a perforate grill 422. The outlet portion 413 continues as a cylindrical neck 415, adapted to receive an end cap 318 of a capsule 310. The neck 415 joins a socket portion 417 of oblong cross section and larger cross sectional size than the neck 415. A transverse shoulder 419 is defined between the neck 415 and the socket 417; internally, the face of the shoulder 419 facing into the socket 417 is adapted to act as a stop for the radial flange 332 of an end cap 318. One or more through holes 421 are formed in the shoulder 419, to define air inlets as described hereafter.

The mouth piece 412 preferably includes turbulence inducing means to create turbulence in air as it passes through the mouth piece. In the illustrated embodiment the turbulence inducing means comprises a stationary turbine 440 in the neck 415 and a through hole 441 in the wall of the neck 415. In other embodiments only one of the turbine 440 and through hole 441 is used.

The dispenser further comprises a tail piece 414 of oblong cross section. The tail piece has a plug portion 423 adapted to be a friction fit in the socket 417. The plug portion 423 is connected to a terminal portion 425. A pair of "L" shaped slots 427, 427', normally diametrically opposed, are defined in the wall of the plug 423. The slots 427, 427' are open at the free end of the plug 423 to receive the radial lugs 313, 313' of the capsule end cap 316 in a bayonet connection.

Figure 15:
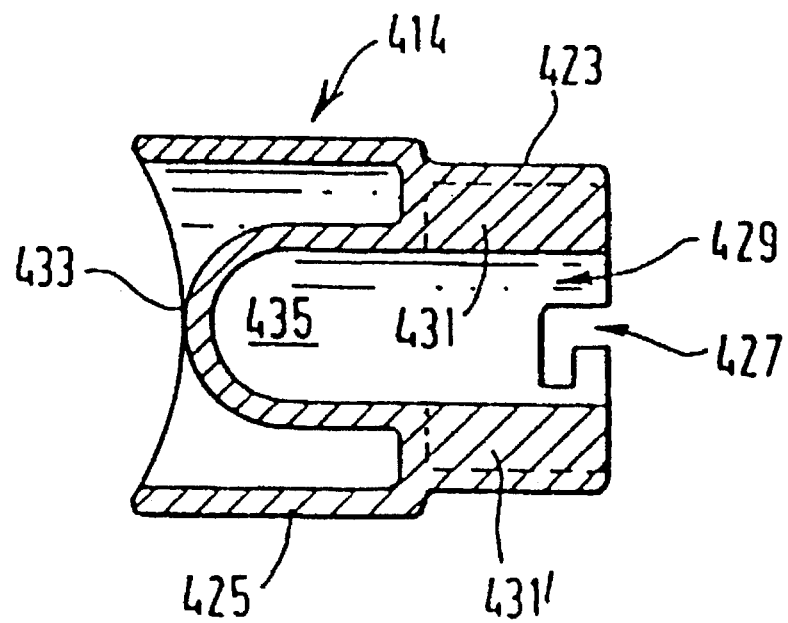
FIG. 15 is a longitudinal cross section through the tail piece of the drug dispenser of FIG. 12.

Internally, the plug portion 423 defines an oblong bore 429 (FIG. 15). Longitudinal retaining ribs 431, 431' are provided on the internal surface of the plug portion 423, whereby the free cross section of the bore 429 in its wide direction is reduced. If appropriate, further retaining ribs (not shown) may be provided, for example equidistant between the ribs 431, 431'.

The bore 429 continues into the terminal portion 425 of the tail piece as a cylindrical bore with a diameter normally substantially the same as that of the free cross section of the bore 429 in the plug portion 423. The bore of the terminal portion 425 is closed by a hemispherical or dome-shaped end wall 433, whereby a back chamber 435 is defined in the terminal portion 425.

In use, a capsule 310 (or other compatible capsule) is fitted into the tail piece 414 and held by the bayonet connections provided (lugs 313, 313'; slots 427, 427'). The plug 423 of the tail piece 414 is pressed into the socket 417 of the mouth piece 412 until the flange 332 of the end cap 318 of the capsule 310 abuts the shoulder 419 of the mouth piece 412. The dispenser then looks as shown in FIG. 13.

The capsule 310 is now held in the dispenser with the end cap 316 held against axial movement into the bore 429 of the tail piece 414 by the lugs 313, 313' in the slots 427, 427', the base of the slot defining abutment surfaces 439, 439' for the lugs 313, 313'. The end cap 318 is held against axial movement into the bore of the mouth piece neck 415 by the shoulder 419 in abutment with the flange 332. When the mouth piece 412 and the tail piece 414 are further pushed towards one another, therefore, the end caps 316, 318 are pushed towards the central flange 314 of the capsule 310 and, in the process, their frangible end faces are cut by the free ends of the body 312 as described with reference to FIGS. 1 to 5.

The patient places the outlet 413 into his mouth and inhales. Air is consequently drawn into the dispenser through the inlets 421 and in an axial direction along the channel defined between the capsule 310 and the wall defining the bore 429. When the air encounters the dome-shaped end wall 433 it is caused to become turbulent. The turbulent air passes through the body 312 of the drug capsule 310 where it entrains a finely divided drug. The air stream with its entrained drug is again caused to become turbulent when it passes through the mouth piece by virtue of the turbine 440 and through hole 441. The turbulence helps ensure that any clumps of powder are broken up, so that the drug is delivered to the patient in finely divided form.

After use, the tail piece 414 and the mouth piece 412 are separated and the used capsule 310 removed. The bayonet connection between the capsule 310 and the tail piece 414 facilitates removal of the capsule 310 by holding the capsule 310 in the tail piece 414, from which it projects. In contrast, the capsule 310 would remain wholly within the mouth piece 412 and could be difficult to remove.

The drug dispenser is preferably provided with a cap 437 (FIG. 14), which is a snap fit or friction fit over the outlet portion 409, and preferably closes the inlet ports 421 as well as the outlet portion. The cap is desirably provided with a clip 437 to help retain the dispenser in a pocket.

In modifications of the dispenser of FIGS. 12 to 15, stop means are provided in the tail piece to abut the radial flange 324 of the capsule end cap 316. For example, the retaining ribs 431, 431' (and any additional retaining ribs) may extend further transversely into the cross section of the bore 429 and be truncated axially at their free ends, such that the free tips of their axial end faces are arranged to abut the flange 324.

In other embodiments, alternative means are provided for removably holding the capsule 310 in the tail piece 414. In some embodiments, the socket 417 is provided on the tail piece 414 and the plug 423 on the mouth piece 412.

In yet further embodiments, the plug 423 and the socket 417 are circular in cross section and are screw threaded, whereby they may be moved together and apart by screw action.

In some variants the dispenser includes baffles or other means to induce turbulence in addition to or as an alternative to the turbulence inducing means constituted by the dome shape of the end wall 433.

An arrangement in which a single opening is formed for release of a drug from a chamber is embodied in the drug dispenser 100 illustrated in FIGS. 16, 16a and 17, 17a. Dispenser 100 includes upper and lower shells 102, 104, respectively which form between them a chamber 106 having a drug dispensing passageway 108 formed therein. At one of its ends the dispenser is formed with an air intake opening 110 communicating with passageway 108 via a tortuous feed channel 112 shaped to induce turbulent induction of air into the passageway 108. At its opposite end the dispenser is formed with a mouth piece 114 incorporating a grid 116 which is formed from cooperating parts of the upper and lower shells.

Figure 16:
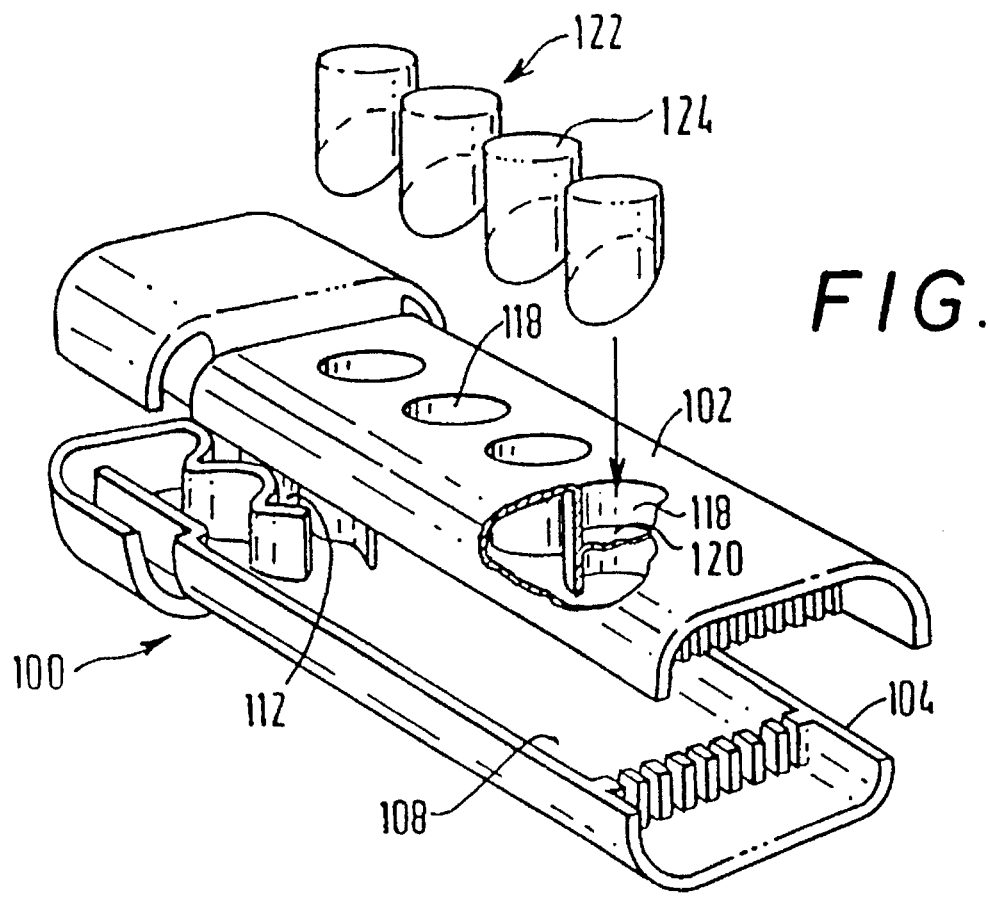
Figure 16A:
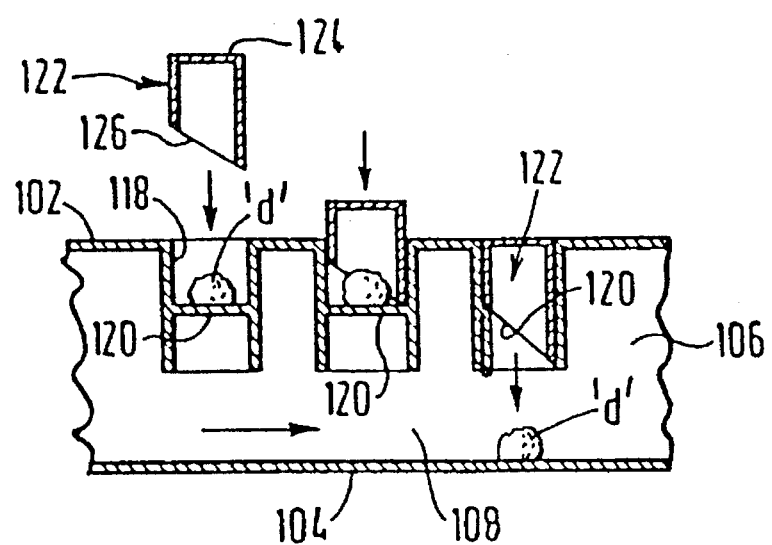
Figure 24:
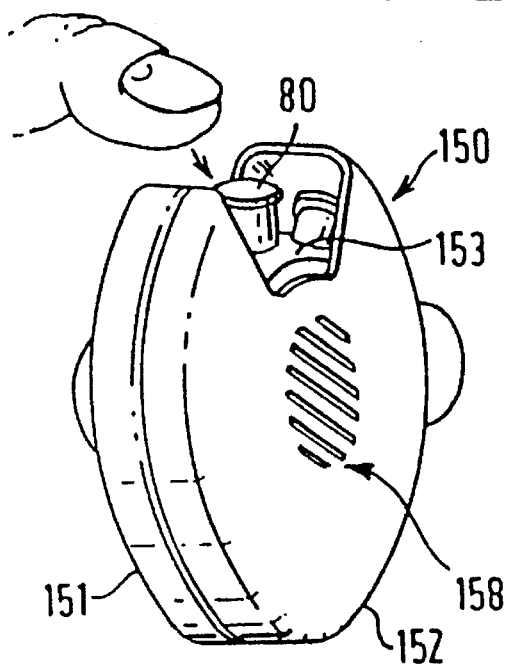
FIG. 24 is a perspective view from one end of a second drug dispenser incorporating a carousel useful with the capsules of FIGS. 18 and 19.
Figure 25:
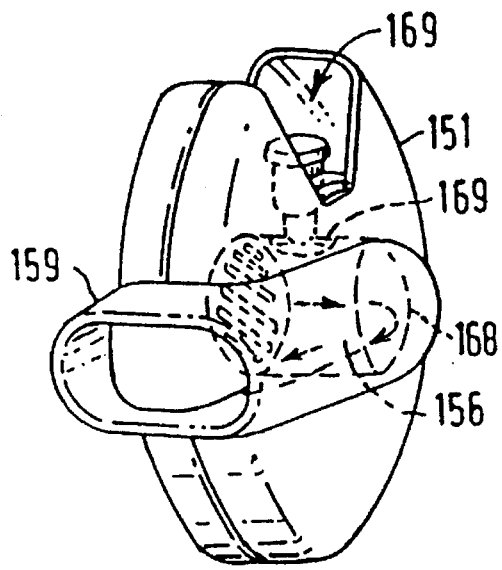
FIG. 25 is a perspective view from the other end of the dispenser of FIG. 24, showing in broken lines its internal structure.
Figure 26:
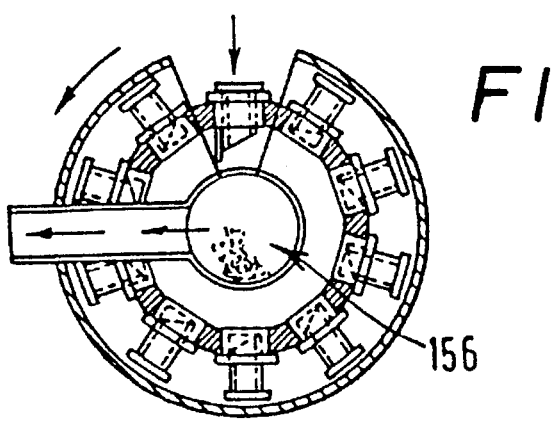
FIG. 26 is a schematic cross section though the dispenser of FIG. 24.
Figure 27:
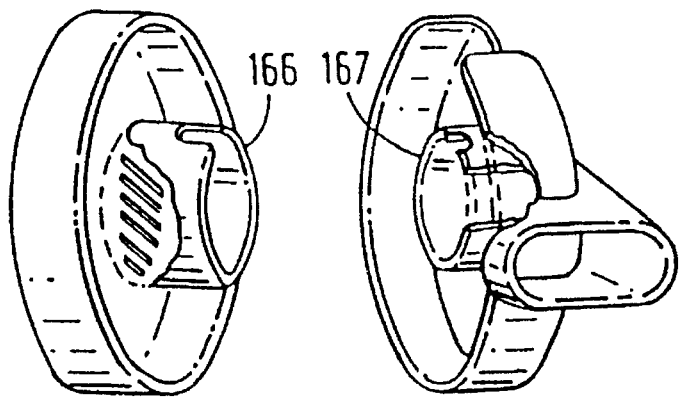
FIG. 27 is an exploded view of the dispenser of FIG. 24, omitting the carousel for clarity.

The upper shell 102 is formed with a row of cylindrical bores 118 each of which is partitioned intermediate its ends by a frangible membrane 120. A drug dosage 'd' is accommodated upon the membrane 120 and the dosage is enclosed in a compartment completed by end cap 122. One end 124 of the end cap stands proud of the top face of the upper shell and the opposite end is obliquely cut-away at 126 so as to readily rupture the membrane when the end cap is depressed into the cylindrical bore (FIG. 16). Once the membrane is thus ruptured, the drug dosage supported by the membrane falls into the passageway 108 and can then be entrained in an airflow created by a patient inhaling through the mouth piece of the dispenser.

Referring now to FIGS. 18 and 19 of the drawings there is shown a single end opening drug capsule 80 comprising a tubular body 90 having an obliquely cut-away end 92 and an opposite end sealed at its end face 94. The cut-away end is normally sealed by end cap 96 having an outwardly extending flange 97 and a frangible end face 98. The body and end cap are axially movable relative to one another in order to open the capsule as previously described.

The single end opening capsule 80 may be used in a modified version of the drug dispenser 100 of FIGS. 16, 16a and 17, 17a. In the modified drug dispenser, the membrane 120 in each bore 118 is replaced by an annular seat on which sits the flange 97 of the end cap 96 of a drug capsule 80 when the capsule is accomodate in the bore 118. The drug capsule 80 may then be ruptured by depressing the end face 94 of the tubular body 94.

The single end opening capsule 80 may alternatively be used in a drug dispenser comprising a rotary capsule carrier or carousel, as illustrated in FIGS. 20 to 23.

FIGS. 20 to 23 show in schematic form a rotary drug dispenser or inhaler 50. The rotary dispenser 50 comprises an upper shell 51 and lower shell 52, which define between them a chamber to receive a carousel or rotary capsule carrier 53. The lower shell 52 is provided with a central boss 54 on which the carousel 53 is adapted to sit for rotation within the chamber of the drug dispenser. Normally, a one-way ratchet mechanism is provided between the carousel 53 and the shell 51, 52 of the drug dispenser, for example between the boss 54 and the corresponding hole 55 in the carousel.

Internally of the dispenser 50, there is defined beneath the carousel 53 a space 56 to receive drug powder. The space 56 is separated from the body of the internal chamber of the dispenser 50 by a wall 57 upstanding from the internal face of the lower shell 51. The space 56 communicates with the exterior through one or more inlet ports 58 (two inlet ports are shown in FIG. 20) and an outlet 59. The outlet 59 is formed by cooperating parts of the upper and lower shells 51,52.

As will be appreciated, the space 56 forms part of an air passageway between the inlet ports 58 and the outlet 59.

The upper shell 52 carries a depressable button 60, which is normally held in a raised position by a spring 65 or other biasing means. The button 60 is disposed above the space 56.

The carousel 53 has defined in it a plurality of through holes 61, in annular arrangement. Normally there are at least five through holes 61. Each through hole is adapted to accommodate a single end opening capsule 80 with its flange 97 seated on the carousel 53 to suspend the capsule in its associated hole 61. Whilst the capsules 80 may be separate from each other, they are conveniently linked together into a ring, for ease of handling.

The dispenser 50 is desirably provided with means to indicate when a through hole 61 of the carousel 53 and any associated drug capsule 80 is disposed over the space 56. For example, the ratchet mechanism may be adapted to offer increased resistance to rotation of the carousel 53 when a through hole 61 is located over the space 56.

In order to use the drug dispenser 50, a carousel 53 carrying drug capsules 80 is placed in the dispenser. If necessary, the carousel 53 is turned until a capsule is located over the space 56. The carousel 53 may be turned by any appropriate means. In the illustrated embodiment, the carousel 53 is turned manually by force applied by thumb or finger to the bevelled circumference 62 of the carousel 53.

The circumference 62 of the carousel is exposed to the exterior by an arcuate recess formed in the shell of the dispenser, in this case in the upper shell 52.

When a drug capsule is located over the space 56, and hence under the button 60, the button 60 is depressed and abutment means connected to the button 60 (a pin 63 integral with the button 60 in the illustrated embodiment) is depressed with the button 60 and caused to strike the end face 94 of the tubular body 90 of the capsule 80. The tubular body 90 is therefore depressed and it ruptures the frangible end face 98 of the end cap 96. Powdered drug 64 is discharged into the space 56 and may be inhaled by a user placing the outlet 59 into his/her mouth and inhaling, to create an airflow through the space 56. If desired, the carousel 53 may be rotated again to enable a further capsule 86 to be discharged.

When all the drug capsules 80 in the carousel have been discharged, the upper 51 and lower 52 shells are separated and the capsules 80 are replaced. Optionally, the carousel may be removed and disposed of, and replaced with a new carousel loaded with full capsules 80.

Numerous modifications to the drug inhalation system illustrated in FIGS. 20 to 23 are possible, whilst still retaining the feature of a rotary drug carrier carrying or adapted to carry drug capsules of the invention, which capsules may be ruptured such that drug powder in the capsules becomes included in an airflow passageway to an outlet of the dispenser. For example, the button 60 may be replaced by a hole in the upper shell 51 whereby capsules may be ruptured by direct finger pressure. In some embodiments the rotary mechanism is modified, for example, so that the carousel 53 may be turned by the action of a trigger. If desired, instead of carrying the capsules of FIGS. 18 and 19, the carousel 53 may comprise drug capsules of the type illustrated in FIG. 16a.

One modified rotary drug dispenser is illustrated in FIGS. 24 to 27. The drug dispenser 150 of FIGS. 24 to 27 comprises a carousel 153 adapted to receive single end opening drug capsules 80 in a generally radial orientation. The carousel 153 is housed in a chamber formed between cooperating shells 151, 152. An arcuate slot 169 is formed in the periphery of the dispenser 150 by cooperating recesses in the shells 151, 152. The slot 169 is in a position which is located at the top of the dispenser when it is used and exposes a portion of the carousel as well as any drug capsule 80 housed in the exposed portion of the carousel.

A space 156 is formed centrally within the dispenser 150 by annular walls 166, 167 extending inwardly from the shells 151, 152. The space 156 is part of an airflow passageway between an air inlet 158, formed by a multiplicity of slots in the shell 152, and an air outlet 159. The outlet 159 communicates with the central space 156 through a port 168 defined in the wall of the shell 151.

Each annular wall 166, 167 has at its free end a recess. The recesses cooperate in the dispenser 150 to form a through hole 168 in the annular wall 166, 167 of the central space 156. In normal use, the through hole 168 is upwardly oriented as shown in FIG. 22.

In use, the carousel 153, which may conveniently be associated with a ratchet mechanism, is rotated until a drug capsule 80 is located above the through hole 168, as shown in FIGS. 21–23. The capsule body may than be depressed by the user's finger to rupture the capsule and allow contained drug powder to discharge into the central space 156 for inhalation, as shown in FIG. 23.

The invention also contemplates the use of a rotary carrier or carousel in drug dispensers of the type in which a double end opening drug capsule is ruptured to form part of the airflow passageway.

I claim:

1. A drug capsule comprising a sleeve forming a side wall of the capsule and having first and second ends, said first and second ends being open, a first end cap closing the open first end of the sleeve, said first end cap being displaceable relative to said sleeve, the first end cap having a first end face which can be ruptured by the first end of the sleeve by urging the first end cap against the first end of the sleeve to open the capsule by at least partially severing the first end face to form a disc of material, the second open end of the sleeve being closed by a rupturable second end cap in like manner to the first end, the second end cap being displaceable relative to said sleeve and comprising a second end face which can be ruptured by the second end of the sleeve by urging the second end cap against the second end of the sleeve to open the capsule by at least partially severing the second end face to form a second disc of material.

2. A drug capsule according to claim 1, wherein the first and second ends of the sleeve comprise respective ellipses, the plane of each ellipse being at an angle to a plane normal to the axis of the sleeve so as to form respective first and second cutting edges which can cut progressively through the first and second end faces of the first and second end caps respectively.

3. A drug capsule according to claim 1, wherein the first and second end caps are displaceably connected to the sleeve by respective rib and groove connections.

4. A drug capsule according to claim 1, wherein the first and second end faces of the end caps remain hinged to the respective first and second end caps after being ruptured and displaced along the sleeve.

5. A drug capsule according to claim 1 formed from a plastics material.

6. A drug capsule according to claim 1, wherein the sleeve is provided with an outwardly projecting flange or other stop means intermediate its ends, against which the end caps abut when fully displaced along the sleeve from its ends.

7. A dispenser formed from the combination of a capsule according to claim 1 and a pair of elements, the elements each being adapted to receive a separate one of the first and second end caps of the capsule so that the capsule interconnects the elements, and wherein one of the elements provides a mouth piece and the capsule can be ruptured by moving the elements towards one another whereby the ruptured capsule provides a part of an air flow passageway of the dispenser so that in use a dose of powder contained within the capsule can be inhaled through the mouth piece.

8. A dispenser as claimed in claim 7, wherein the other of the elements comprises a tail piece including an end part which forms an elbow in the air flow passageway of the dispenser so that in use powder from the capsule is not lost through an open end of the tail piece.

9. A dispenser according to claim 7, wherein means are provided in said tail piece to induce a turbulent air flow through the dispenser in use.

10. A dispenser as claimed in claim 7, wherein the first and second end caps comprise radially projecting flanges defining abutment surfaces engagable by cooperating abutment surfaces of the elements whereby in use relative displacement of the elements effects relative displacement of the end caps to provide the actuating movement relative to the side wall portion.

\* \* \* \* \*